(12) United States Patent
Shin

(10) Patent No.: US 11,974,940 B2
(45) Date of Patent: May 7, 2024

(54) MANDIBULAR ADVANCEMENT DEVICE

(71) Applicant: SEOUL NATIONAL UNIVERSITY R&DB FOUNDATION, Seoul (KR)

(72) Inventor: Hyun Woo Shin, Seongnam-si (KR)

(73) Assignee: SEOUL NATIONAL UNIVERSITY R&DB FOUNDATION, Seoul (KR)

( * ) Notice: Subject to any disclaimer, the term of this patent is extended or adjusted under 35 U.S.C. 154(b) by 61 days.

(21) Appl. No.: 16/962,103

(22) PCT Filed: Apr. 2, 2020

(86) PCT No.: PCT/KR2020/004507
§ 371 (c)(1),
(2) Date: Jul. 14, 2020

(87) PCT Pub. No.: WO2021/066270
PCT Pub. Date: Apr. 8, 2021

(65) Prior Publication Data
US 2021/0401614 A1    Dec. 30, 2021

(30) Foreign Application Priority Data
Sep. 30, 2019 (KR) .......................... 10-2019-0121070

(51) Int. Cl.
*A61F 5/56* (2006.01)
(52) U.S. Cl.
CPC .................. *A61F 5/566* (2013.01)
(58) Field of Classification Search
CPC ..... A61F 5/566; A61B 5/1116; A61B 5/4542; A61B 5/4818; A61B 5/4836; A61B 5/682; A61B 5/08; A61B 5/1455; A61C 5/007
See application file for complete search history.

(56) References Cited

U.S. PATENT DOCUMENTS 5,826,579 A    10/1998   Remmers et al.
5,921,942 A     7/1999   Remmers et al.
(Continued)

FOREIGN PATENT DOCUMENTS

JP    2012-528698 A    11/2012
KR    2012-0099402 A    9/2012
(Continued)

OTHER PUBLICATIONS

First Examination Report dated Dec. 23, 2020 in Australian Patent Application No. 2020204643, filed Apr. 2, 2020, 7 pages.
(Continued)

*Primary Examiner* — Kim M Lewis
(74) *Attorney, Agent, or Firm* — Kilpatrick Townsend & Stockton LLP

(57) ABSTRACT

Provided is a mandibular advancement system including: an upper teeth seating part on which upper teeth of a user is placed; a lower teeth seating part on which lower teeth of the user is placed; a driver connected to the upper teeth seating part and the lower teeth seating part and configured to change a relative location of the lower teeth seating part with respect to the upper teeth seating part; a detector configured to detect biometric information of the user; and a controller configured to control driving of the driver based on the biometric information provided by the detector, wherein the driver is disposed outside an oral cavity of the user.

11 Claims, 12 Drawing Sheets

(56) References Cited

U.S. PATENT DOCUMENTS

| | | | |
|---|---|---|---|
| 7,146,982 B2 | 12/2006 | Mousselon et al. | |
| 11,246,744 B2* | 2/2022 | Shin | A61B 5/4818 |
| 2010/0316973 A1* | 12/2010 | Remmers | A61F 5/566 |
| | | | 433/214 |
| 2018/0228644 A1* | 8/2018 | Shin | A61B 5/682 |

FOREIGN PATENT DOCUMENTS

| | | |
|---|---|---|
| KR | 10-1722640 B1 | 4/2017 |
| KR | 10-1784416 B1 | 11/2017 |
| KR | 10-1911279 B1 | 10/2018 |
| WO | 2014-159236 A2 | 10/2014 |
| WO | 2015-187949 A1 | 12/2015 |

OTHER PUBLICATIONS

Office Action dated Feb. 23, 2021 in Korean Patent Application No. 10-2019-0121070, filed Oct. 25, 2019, 8 pages.

* cited by examiner (a)

(b)

MOVEMENT DIRECTION
OF LOWER JAW

MANDIBULAR ADVANCEMENT DEVICE

TECHNICAL FIELD

The present disclosure relates to a mandibular advancement device.

BACKGROUND ART

In general, when muscles surrounding a person's airway are relaxed during sleep, the uvula, tonsils, tongue, etc. may fall back. Thus, the tonsils may become narrower than in daytime, but most people do not have problems. However, some people may have airways that become seriously narrow during sleep and prevent air from passing through, and thus, snoring and obstructive sleep apnea (OSA) occurs. Snoring and OSA may be caused when the airway is partially blocked or other problems exist because the jaw of a person is smaller than normal, the tongue or tonsils are large, or the uvula is stretched.

A variety of intraoral apparatuses or methods have been used to relieve snoring and OSA. For example, the above methods include a method of expanding a narrow airway by using an apparatus for moving lower jaw forward.

FIG. 1 illustrates a dental appliance for treatment of snoring and OSA according to the related art. A mandibular advancement device 1 is included in an intraoral dental appliance worn by a patient to secure the airway in the upper pharynx, and includes an upper member 11 disposed according to a set of teeth in the upper jaw of the patient, a lower member 12 disposed according to a set of teeth in the lower jaw of the patient, a connector 13 extending to be firmly connected to the upper member 11 and a bottom surface extending from the upper member 11, and slots 14 that are apart from each other to be in parallel with the lower member 12. As the connector 13 is selectively inserted into any one of the slots 14, the upper member 11 and the lower member 12 are connected to each other to make the lower member 12 be located at a front portion that protrudes relative to the upper member 11.

DESCRIPTION OF EMBODIMENTS

Technical Problem

One or more embodiments of the disclosure provide a mandibular advancement system that determines whether to move a mandibular advancement device based on a sleep position, respiratory sound (breathing sound), oxygen saturation, body movements, and the like to detect a sleep position of a patient having a snoring problem and sleep apnea during sleep.

Solution to Problem

According to an aspect of the present disclosure, provided is a mandibular advancement system including: an upper teeth seating part on which upper teeth of a user is placed; a lower teeth seating part on which lower teeth of the user is placed; a driver connected to the upper teeth seating part and the lower teeth seating part and configured to change a relative location of the lower teeth seating part with respect to the upper teeth seating part; a detector configured to detect biometric information of the user; and a controller configured to control driving of the driver based on the biometric information provided by the detector, wherein the driver is disposed outside an oral cavity of the user.

Advantageous Effects of Disclosure

A mandibular advancement system according to embodiments of the disclosure determines whether to move a mandibular advancement device according to a sleep position, by detecting a sleep position of a patient having a snoring problem and sleep apnea during sleep. Also, because a driver is disposed outside, the mandibular advancement system may decrease a pain and drooling caused when the user wears the mandibular advancement device, and may provide a sufficient amount of power to move the lower jaw forward.

BEST MODE

Figure 1:
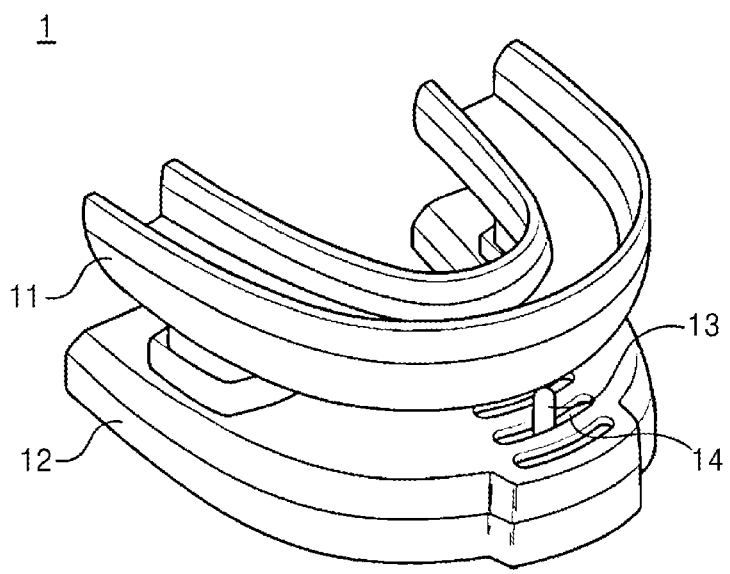
FIG. 1 is a diagram of a mandibular advancement device according to the related art.

According to an embodiment, there is provided a mandibular advancement system including: an upper teeth seating part on which upper teeth of a user is placed; a lower teeth seating part on which lower teeth of the user is placed; a driver connected to the upper teeth seating part and the lower teeth seating part and configured to change a relative location of the lower teeth seating part with respect to the upper teeth seating part; a detector configured to detect biometric information of the user; and a controller configured to control driving of the driver based on the biometric information provided by the detector, wherein the driver is disposed outside an oral cavity of the user.

The mandibular advancement system may further include a body portion including a surface disposed apart from the upper teeth seating part or the lower teeth seating part by a certain distance and housing the driver.

The upper teeth seating part and the lower teeth seating part may be disposed outside the body portion.

The detector may be disposed in the body portion.

The detector may include at least any one of a respiration sensor, an oxygen saturation sensor, and a posture sensor.

The controller may be configured to determine a sleep state of the user based on the biometric information and control the driving of the driver according to the sleep state.

The driver may include a driving power unit configured to generate driving power and a driving power transmission unit configured to transmit the driving power generated by the driving power unit to the upper teeth seating part or the lower teeth seating part.

The driving power unit may include a pump configured to inject air into the driving power transmission unit, and the driving power transmission unit may include a cylinder configured to accommodate the air injected from the pump and a piston that is movable due to the air in the cylinder.

The driving power transmission unit may further include a tube that is a passage for the air injected from the pump, and the detector may include a pressure sensor configured to detect pressure in the tube.

The cylinder may be connected to the lower teeth seating part, and the piston may be connected to the upper teeth seating part.

The driving power transmission unit may further include an elastic member configured to provide a restoration force between the piston and the cylinder.

Other aspects, features, and advantages other than those described above will become apparent from the following detailed description, claims and drawings for carrying out the disclosure.

Mode of Disclosure

As the disclosure allows for various changes and numerous embodiments, particular embodiments will be illustrated in the drawings and described in detail in the written description. The attached drawings for illustrating preferred embodiments of the present disclosure are referred to in order to gain a sufficient understanding of the present disclosure, the merits thereof, and the objectives accomplished by the implementation of the present disclosure. The disclosure may, however, be embodied in many different forms and should not be construed as being limited to the embodiments set forth herein.

The present disclosure will now be described more fully with reference to the accompanying drawings, in which exemplary embodiments of the disclosure are shown. Like reference numerals in the drawings denote like elements, and thus their description will be omitted.

It will be understood that although the terms "first," "second," etc. may be used herein to describe various components, these components should not be limited by these terms. These components are only used to distinguish one component from another.

As used herein, the singular forms "a," "an" and "the" are intended to include the plural forms as well, unless the context clearly indicates otherwise.

It will be further understood that the terms "comprises" and/or "comprising" used herein specify the presence of stated features or components, but do not preclude the presence or addition of one or more other features or components.

Sizes of components in the drawings may be exaggerated for convenience of explanation. In other words, since sizes and thicknesses of components in the drawings are arbitrarily illustrated for convenience of explanation, the following embodiments are not limited thereto.

Figure 2:
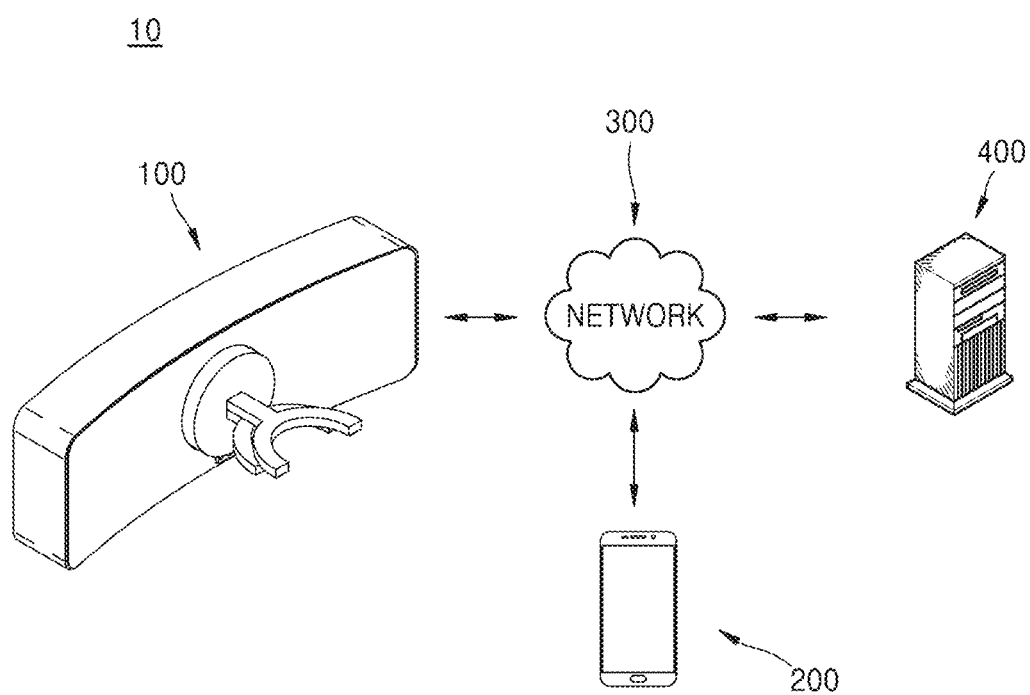
FIG. 2 is an example of a network environment according to an embodiment of the present disclosure.
Figure 3:
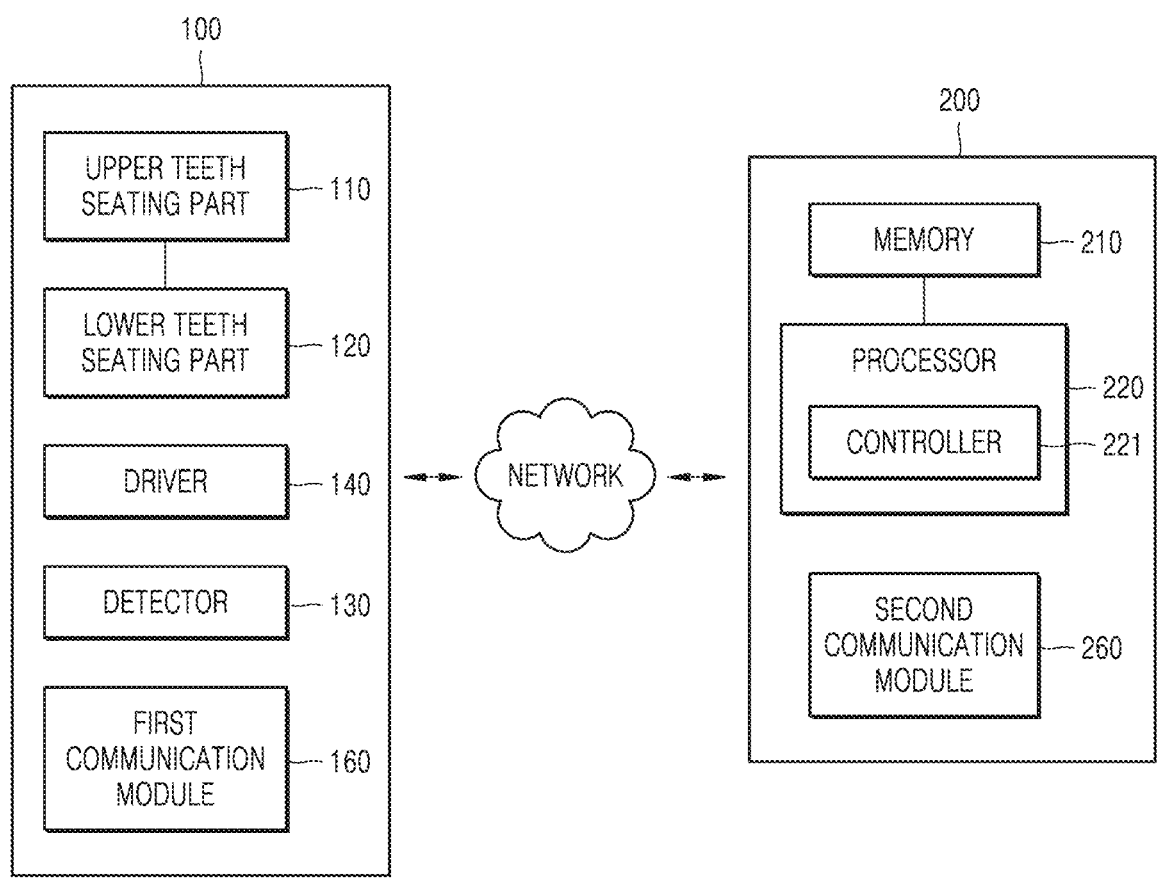
FIG. 3 is a schematic block diagram of a mandibular advancement system according to an embodiment of the present disclosure.

FIG. 2 is an example of a network environment according to an embodiment of the present disclosure, and FIG. 3 is a schematic block diagram of a mandibular advancement device 100 according to an embodiment of the present disclosure.

The network environment of FIG. 2 may include a mandibular advancement device 100, a user terminal 200, a server 400, and a network 300. The network environment of FIG. 2 is an example, and the number of mandibular advancement devices 100 and the number of user terminals 200 are not limited as illustrated in FIG. 2.

In an embodiment, while the user wears the mandibular advancement device 100 during sleep, the mandibular advancement system 10 using the network environment of FIG. 2 may detect biometric information of a user and move the lower jaw according to a sleep state of the user that is determined based on the detected biometric information. Thus, snoring or sleep apnea may be relieved, depending on each user. In this case, a driver 140 is disposed outside the oral cavity but inside a body portion 103 that is portable, and thus the mandibular advancement device 100 may increase the convenience of the user because the user may wear the mandibular advancement device 100 during sleep without a separate connection with an external device. At the same time, the mandibular advancement device 100 may obtain accurate biometric information about sleep.

Referring to FIGS. 2-5, the mandibular advancement device 100 may include the body portion 103 disposed outside the oral cavity while the user wears the mandibular advancement device 100, and may include an upper teeth seating part 110 and a lower teeth seating part 120 disposed on the oral cavity to move the lower jaw of the user according to the sleep state while the user wears the mandibular advancement device 100. The mandibular advancement device 100 may maximize the portability and convenience as the driver 140 is disposed outside and the driver 140 and a power supply unit 150 are integrally formed in the body portion 103. Also, the mandibular advancement device 100 may detect the biometric information of the user by using a detector 130 and may provide the biometric information to the user terminal 200 or the server 400 through the network 300. The mandibular advancement device 100 will be described below in detail.

The user terminal 200 may be a fixed terminal or a portable terminal realized as a computer device. The user terminal 200 may be a terminal that performs a function of controlling the mandibular advancement device 100 based on the biometric information received from the mandibular advancement device 100 or transmits the biometric information to the server 400. The user terminal 200 may be, for example, a smart phone, a mobile phone, a navigation device, a computer, a laptop computer, a digital broadcasting terminal, a personal digital assistant (PDA), a portable multimedia player (PMP), a tablet PC, or the like. For example, the user terminal 200 may communicate with another user terminal and/or the server 400 through the network 300 in a wireless or wired communication manner.

The communication manner is not limited and may include a communication manner using a network (e.g., a mobile communication network, wired Internet, wireless Internet, a radio network) that may be included in the network 300 as well as a short-range wireless communication between devices. For example, the network 300 may include at least one arbitrary network from among a personal area network (PAN), a local area network (LAN), a campus area network (CAN), a metropolitan area network (MAN), a wide area network (WAN), a broadband network (BBN), and the Internet. Also, the network 300 may include at least arbitrary one of network topologies including a bus network, a star network, a ring network, a mesh network, a star-bus network, a tree or hierarchical network, and the like, but is not limited thereto.

The server 400 may communicate with the user terminal 200 or the mandibular advancement device 100 through the network 300 and may be realized as a computer device or computer devices providing commands, code, files, content, service, or the like.

For example, the server 400 may provide a file for installing an application, to the user terminal 200 connected through the network 300. In this case, the user terminal 200 may install an application by using the file provided by the server 400. Also, an access to the server 400 may be allowed according to the control of an operating system (OS) and at least one program (e.g., a browser or an installed application) included in the user terminal 200, and service or content provided by the server 400 may be received. As another example, the server 400 may set a communication session for data reception/transmission and may perform routing for the data reception/transmission between the user terminals 200 through the set communication session.

The server 400 according to an embodiment includes a controller, and when the biometric information of the user is provided, the server 400 may determine a sleep state of the user based on the biometric information, determine when or how much the lower jaw is to be moved according to a determination result, generate a control signal for controlling the driver 140 of the mandibular advancement device 100, and provide the generated control signal to the user terminal 200 or the mandibular advancement device 100. Also, when the biometric information of the user is regularly provided, the server 400 may train for determination criteria used to determine the sleep state of the user based on the biometric information, generate a control signal corresponding to the sleep state of the user based on a determination result, and provide the control signal to the user terminal 200 or the mandibular advancement device 100, thereby re-training the determination criteria or control signal generation criteria based on the biometric information that is fed back.

However, one or more embodiments of the disclosure are not limited thereto, and the controller performing the above function may be disposed in the user terminal 200 or the mandibular advancement device 100 instead of the server 400. Also, the server 400 may train for the sleep state determination criteria and the control signal generation criteria based on deep learning, transmit the sleep state determination criteria and the control signal generation criteria to the mandibular advancement device 100 or the user terminal 200 to directly determine the sleep state of the user in the mandibular advancement device 100 or the user terminal 200, and generate the control signal. Hereinafter, for convenience, a case where the controller 221 is included in the user terminal 200 will be mainly described.

Figure 4:
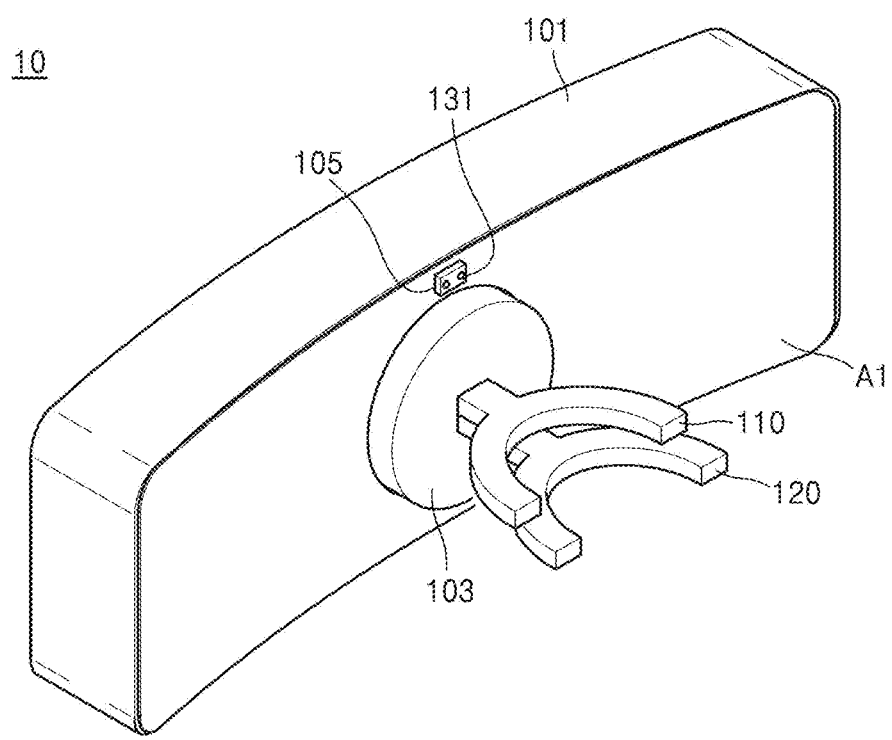
FIG. 4 is a perspective view of a mandibular advancement device according to an embodiment of the present disclosure.
Figure 5:
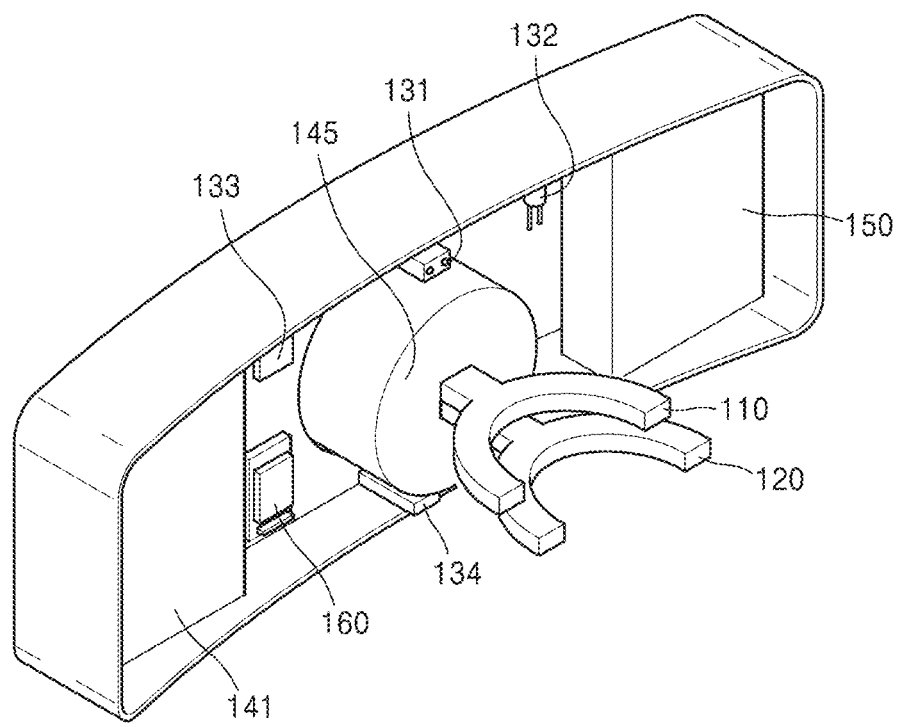
FIG. 5 is diagram for explaining an internal structure of the mandibular advancement device of FIG. 4.

FIG. 4 is a perspective view of the mandibular advancement device 100 according to an embodiment of the present disclosure, and FIG. 5 is diagram for explaining an internal structure of the mandibular advancement device 100 of FIG. 4.

Referring back to FIG. 3 and to FIGS. 4 and 5, the mandibular advancement system 10 according to an embodiment may include the upper teeth seating part 110, the lower teeth seating part 120, the detector 130, the driver 140, and the controller 221. In this case, the upper teeth seating part 110, the lower teeth seating part 120, the detector 130, and the driver 140 may be included in the mandibular advancement device 100 that the user wears, and the controller 221 may be included in the user terminal 200.

The mandibular advancement device 100 may include the upper teeth seating part 110, the lower teeth seating part 120, the detector 130, and the driver 140 and may further include a body portion 101, the power supplier 150, and a communication module 160.

The upper teeth seating part 110 may be mounted on upper teeth of the user. The upper teeth of the user may be inserted into the upper teeth seating part 110. The upper teeth seating part 110 may be customized according to a set of user's teeth to reduce irritation or inconvenience when the upper teeth is mounted. The upper teeth seating part 110 may surround the upper teeth and adhere thereto when mounted on the upper teeth.

The lower teeth seating part 120 may be mounted on lower teeth of the user. The lower teeth seating part 120 may be customized according to a set of user's teeth to reduce irritation or inconvenience when the lower teeth is mounted. The lower teeth seating part 120 may surround and adhere to the lower teeth when mounted on the lower teeth.

The driver 140 may be connected to the upper teeth seating part 110 and the lower teeth seating part 120 and may change a relative location of the lower teeth seating part 120 with respect to the upper teeth seating part 110. The driver 140 may include a driving power unit 141 providing driving power and a driving power transmission unit 145 transmitting the driving power, which is generated by the driving power unit 141, to the upper teeth seating part 110 or the lower teeth seating part 120.

Any means for generating the driving power may be used as the driving power unit 141. For example, the driving power unit 141 may generate the driving power by using any one of a motor, an actuator, and a pump. Alternatively, the driving power unit 141 may generate the driving power by using an electromagnet or a shape-memory alloy.

The driving power transmission unit 145 may include a transmission means corresponding to a type of the driving power unit 141. For example, when the driving power unit 141 is a motor or an actuator, the driving power transmission unit 145 may include at least one gear capable of transmitting the driving power generated from the motor or the actuator. Alternatively, in another embodiment, when the driving power unit 141 is a pump, the driving power transmission unit 145 may include a cylinder and a piston for transmitting flow of air generated from the pump. The driver 140 according to another embodiment will be described below.

The driver 140 may be disposed outside the oral cavity of the user. In this case, the driver 140 may be disposed outside the oral cavity while housed in the body portion 103. Because the driver 140 is disposed outside the oral cavity, problems such as a limitation in the size of a structure due to the volume limit in the oral cavity, or a failure to generate enough power to move the lower jaw, may be solved. When the driver 140 is disposed outside the oral cavity, the driving power unit 141 for providing power for moving the lower jaw forward may be easily selected, and the detector 130 and the like, which are disposed in the driving power transmission unit 145, may be freely selected. As the selection may be freely made, the performance of the detector 130 may be improved. Also, the irritation that the user feels may be reduced, and noise which may disturb the sleep may also be reduced.

The body portion 101 may form the appearance of the mandibular advancement device 100 and may include a surface A1 that is disposed apart from the upper teeth seating part 110 or the lower teeth seating part 120 by a certain distance. When the user wears the mandibular advancement device 100, the body portion 101 may have at least the surface A1 having a certain curvature to correspond to a mouth portion of the user. The surface A1 may have a curvature corresponding to a facial shape of the user, more particularly, to a shape of the mouth portion. As illustrated in the drawing, the body portion 101 may entirely be formed in a curved-line form. In other words, a surface opposite to the surface A1 may also have a curved portion having the same curvature as the surface A1.

Also, the body portion 101 may further include a protruding body portion 103 that separately houses therein the driving power transmission unit 145 connected to the upper teeth seating part 110 and the lower teeth seating part 120 which are disposed outside the body portion 101. While realizing a function of housing the driving power transmission unit 145 therein, the protruding body portion 103 may realize a function of minimizing the inconvenience caused when the surface A1 contacts the mouth or skin of the user, by allowing the surface A1 to be apart from the oral cavity or mouth of the user by a certain distance.

The body portion 101 may include a through hole 105 in the surface A1 to secure a sensing area of an oxygen saturation sensor 131 included in the detector 130. When the user wears the mandibular advancement device 100, the through hole 105 may be formed at a higher level than the protruding body portion 103 to be close to a nose.

The detector 130 may detect the biometric information of the user. The detector 130 may include various sensors for detecting the biometric information used to determine whether the user sleeps, a sleep posture, and a sleep state such as snoring or sleep apnea. For example, the detector 130 may include at least one of a respiration sensor 132, the oxygen saturation sensor 131, and posture sensors 133 and 134.

The respiration sensor 132 may be a sound sensor capable of detecting snoring sound or an air flow sensor for detecting user's breath inhaled or exhaled through the mouth or nose. The oxygen saturation sensor 131 may be a sensor for detecting the oxygen saturation. The respiration sensor 132 and the oxygen saturation sensor 131 may obtain the biometric information used to determine the sleep state such as snoring or sleep apnea of the user.

The posture sensors 133 and 134 may be sensors for detecting the biometric information used to determine a sleep position of the user. The posture sensors 133 and 134 may be integrally formed, but as illustrated in the drawing, the posture sensors 133 and 134 of different types may be disposed at different locations and obtain the biometric information. For example, the posture sensors 133 and 134 may include a triaxial sensor 133. The triaxial sensor 133 may be a sensor for detecting changes of a yaw axis, a pitch axis, and a roll axis. The triaxial sensor 133 may include at least one of a gyroscope sensor, an acceleration sensor, and a tilt sensor. Also, one or more embodiments are not limited thereto, and a sensor for detecting a change in axes having a different number from a tri-axis may be applied.

The detector 130 may be disposed inside or outside the oral cavity, and hereinafter, for convenience, a case where the detector 130 is disposed outside the oral cavity, that is, in the body portion 101, will be described. The biometric information may be transmitted to the user terminal 200 through a first communication module 160 disposed inside the body portion 101. Here, the communication module 160 may include a communication means capable of communicating with the user terminal 200, for example, Bluetooth, ZigBee, Medical Implant Communication Service (MISC), or Near Field Communication (NFC).

Also, the power supplier 150 may be disposed in the body portion 101. The power supplier 150 may include a replaceable or rechargeable battery.

Because the mandibular advancement device 100 having the above structure is integrally formed, the user may freely sleep without an interference with wire, etc. during sleep.

The user terminal 200 may include a memory 210, a processor 220, and a second communication module 260 (see FIG. 3).

The memory 210 may be a computer-readable recording medium and may include a permanent mass storage device such as random access memory (RAM), read only memory (ROM), and a disk drive. Also, in the memory 210, an OS and at least one program code (e.g., code for the browser or the application installed and executed in the user terminal 200) may be stored. Such software components may be located from a computer-readable recording medium that may be read by a computer separate from the memory 210 by using a drive mechanism. The computer-readable recording medium that may be read by a separate computer may include floppy drives, disks, tapes, DVD/CD-ROM drives, memory cards.

In another embodiment, the software components may be loaded not from the computer-readable recording medium but from the memory 210 through the second communication module 260. For example, at least one program may be loaded on the memory 210 based on a program (e.g., the application) installed using files provided through the network 300 from developers or a file distribution system (e.g., the server 400) for distributing an application installation file.

The processor 220 may execute commands of a computer program by performing a basic arithmetic operation, logic, and input/output operations. Here, the term 'processor' may denote, for example, a data processor embedded in hardware and having a physically-structured circuit to perform functions expressed in code or commands included in a program. Examples of a data processor embedded in hardware may include a microprocessor, a central processing unit (CPU), a processor core, a multiprocessor, an application-specific integrated circuit (ASIC), a field programmable gate array (FPGA), and the like, but one or more embodiments are not limited thereto. The commands may be provided to the processor 220 by the memory 210 or the second communication module 260. For example, the processor 220 may execute commands received according to program code stored in a recording medium such as the memory 210. The processor 220 may include the controller 221. A method of moving the lower jaw of the user by using the controller 221 will be described below.

Although not illustrated, the user terminal 200 may further include an input/output interface. The input/output interface (not illustrated) may be a medium for interfacing with input/output devices. For example, the input device may include a device such as a keyboard or a mouse, and the output device may include a device such as a display for displaying a communication session of an application. As another example, the input/output interface (not illustrated) may be a medium for interfacing with a device, for example, a touch screen, in which input/output functions are integrated.

The user terminal 200 may display sleep state information of the user, which is recorded during sleep, to the outside through the input/output interface to enable the user to identify the displayed sleep state information.

Hereinafter, referring to FIGS. 6 to 8, a method of moving the lower jaw by using the mandibular advancement system 10 according to an embodiment will be described in detail.

Figure 6:
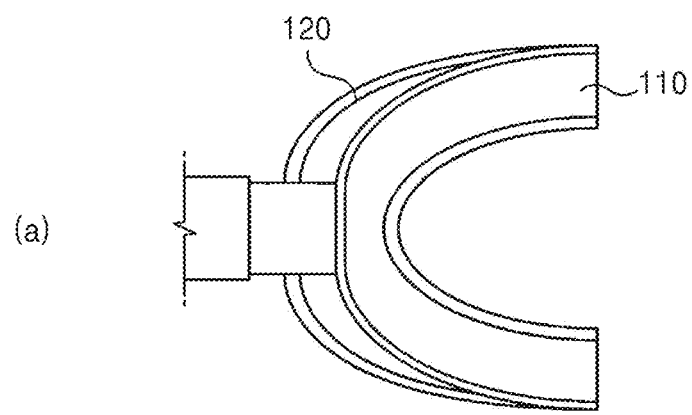
FIG. 6 illustrates a working principle of a mandibular advancement device according to an embodiment of the present disclosure.
Figure 6:
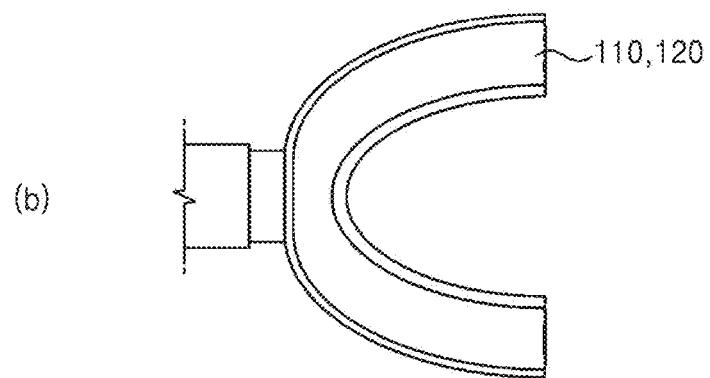

FIG. 6 illustrates a working principle of a mandibular advancement device according to an embodiment of the present disclosure. FIG. 7 illustrates a state in which a mandibular advancement device is used. FIG. 8 is a flowchart of a control method of a mandibular advancement device.

Figure 7:
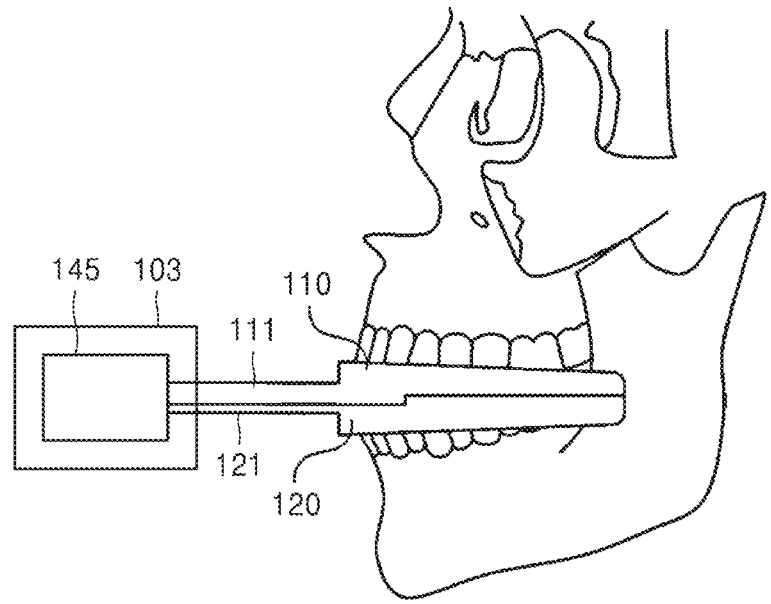
FIG. 7 illustrates a state in which a mandibular advancement device is in use.
Figure 7:
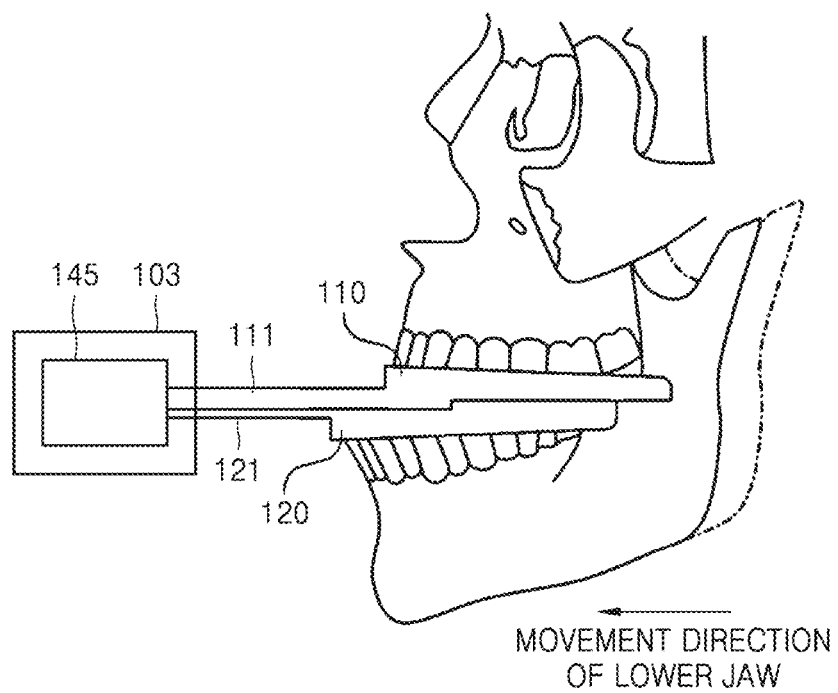
Figure 8:
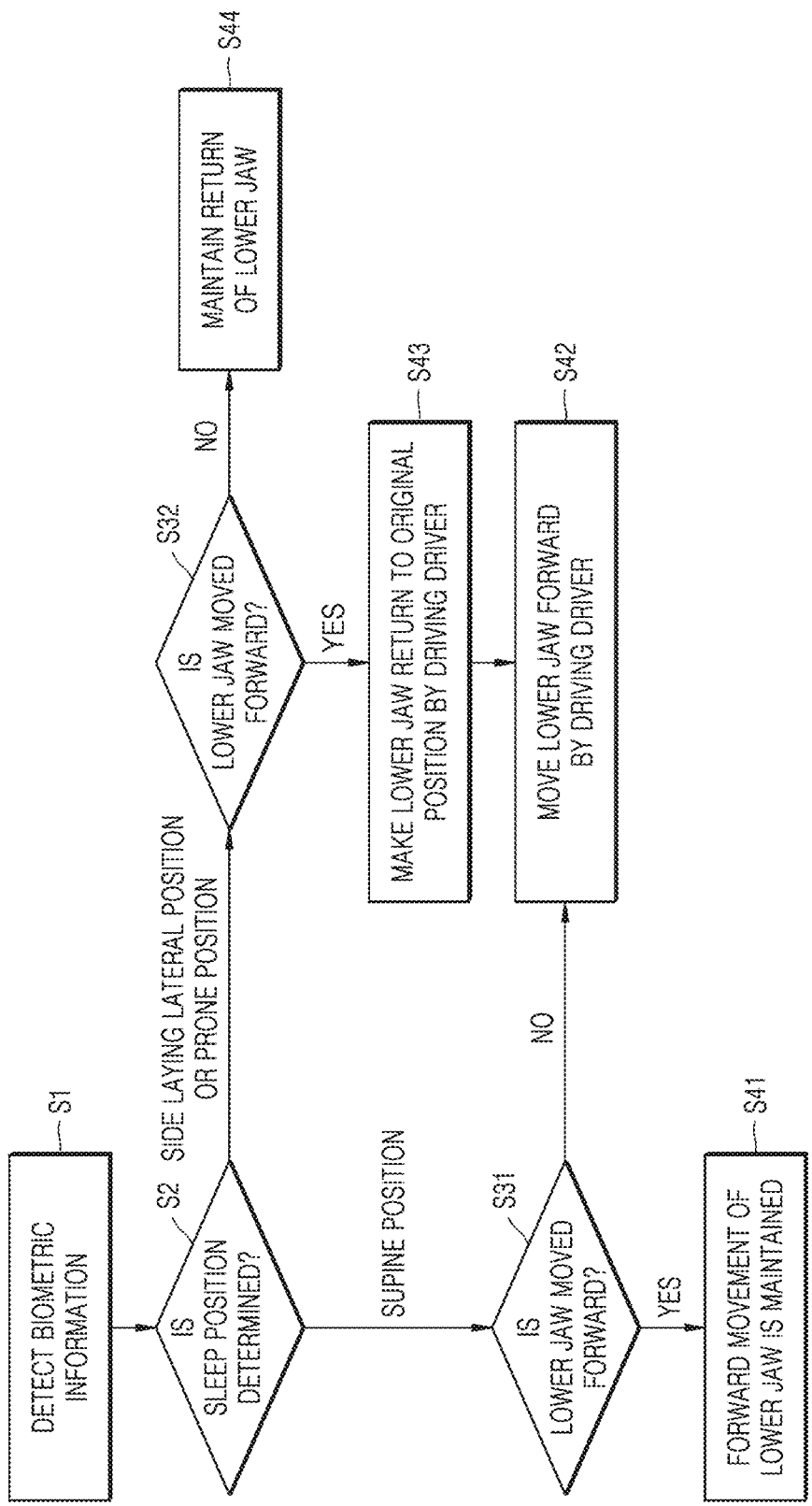
FIG. 8 is a flowchart of a control method of a mandibular advancement device.

Referring to FIGS. 6 to 8, the controller 221 may determine (S2) the sleep state of the user based on the biometric information (S1 of FIG. 8) provided from the detector 130 and may control the operation of the driver 140 according to the sleep state. In more detail, the controller 221 may determine first whether the user actually falls asleep, based on the biometric information detected from the respiration sensor 132 or the oxygen saturation sensor 131. Then, the controller 221 may determine a sleep position of the user based on the biometric information provided from the posture sensors 133 and 134.

Here, the sleep position may denote a posture that is made when the user moves his/her whole body during sleep, but more particularly, a posture of the head in which the internal structure of the airway relatively changes in gravitational space. In other words, although the user may straightly lie down or lie on his/her side during sleep, the head of the user may not just follow the posture, but may lean or be tilted in a direction different form the body, depending on the user. In this case, although the user lies down, the airway that is an air passage may not be secured because the head of the user leans, and thus snoring or sleep apnea may occur. The mandibular advancement system according to an embodiment may detect, as the sleep position, a movement of the user's body as well as a movement of the user's head, which is directly related to breathing, by using the posture sensors 133 and 134 disposed in the body portion 103, and may move the lower jaw according to the sleep position.

The sleep position may at least include a first sleep position and a second sleep position that is different from the first sleep position. That is, when the sleep position is determined as the first sleep position, the lower jaw may be moved by a first distance, and when the sleep position is determined as the second sleep position, the lower jaw may be moved by a second distance different from the first distance. In this case, the first distance and the second distance may not necessarily be in the same direction and may be in different directions. For example, the sleep position may include at least two of a supine position, a side lying lateral position, and a prone position, and as described above, the sleep position may include a movement of the user's head. Also, the controller 221 may detect a certain sleep position according to a sleep disorder degree of the user.

When snoring and sleep apnea occur during sleep, the lower teeth seating part 120 may be moved forward to allow the lower jaw to protrude, as illustrated in FIG. 6(a). When snoring or sleep apnea is determined based on the biometric information detected from the respiration sensor 132 or the oxygen saturation sensor 131, the controller 221 may drive the posture sensors 133 and 134. As described above, because a distance or degree, in which the lower jaw is moved, is changed according to the sleep position, when the snoring or sleep apnea is determined, the controller 221 may additionally obtain the biometric information necessary to determine the sleep position by driving the posture sensors 133 and 134.

The controller 221 may detect a supine position, a side lying lateral position, a prone position, and a certain sleep position and may control the driver 140 according to the sleep position. For example, as illustrated in FIG. 8, in operation S1, the sleep position of the user wearing the mandibular advancement device 100 may be detected. In operation S2, the sleep position may be determined by the detector 130 disposed in the mandibular advancement device 100. In operation S31, when the sleep position is determined as the supine position, a determination as to whether the lower jaw is moved forward may be made. In operation S41, when the lower jaw is moved forward, the forward movement of the lower jaw may be maintained. Alternatively, in operation S42, the lower jaw may be moved forward by driving the driver 140. In operation S32, when the sleep position is determined as the side lying lateral position or prone position, a determination as to whether the lower jaw is moved forward may be made. In operation S43, in a state in which the lower jaw is moved forward, the lower jaw may be returned to its original position by driving the driver. In operation S44, when the lower jaw is returned to its original position, this state may be maintained.

In more detail, when the controller 221 determines that the sleep position is supine position (S31 of FIG. 8), the driver 140 may drive the driving power unit 141 to move the lower teeth seating part 120 forward (S42 of FIG. 8). In a state in which the lower teeth seating part 120 is moved forward, the forward movement may be maintained unless the sleep position of the user is changed to the side lying lateral position or the prone position (S41 of FIG. 8). The airway may be expanded by keeping opening the airway near the pharynx due to the lower teeth seating part 120 that is moved forward, and thus the air may smoothly flow in the airway. Therefore, unlike a case where the lower teeth are moved forward and thus the inconvenience to the jaw or teeth is caused regardless of a conventional sleep position, the forward movement of the lower jaw may differ according to the sleep position of the user.

That is, when the user wearing the mandibular advancement device 100 changes the supine position to the side lying lateral position or the prone position (S32 of FIG. 8), the lower teeth seating part 120 may be returned to its original position with respect to the upper teeth seating part 110 (S43 of FIG. 8). Thus, when the user sleeps in the side lying lateral position or the prone position, the coercive force may not be applied to the lower teeth seating part 120 or the upper teeth seating part 110, and thus a jaw pain of the user may be relieved.

When the mandibular advancement device 100 operates, the forward movement of the lower teeth seating part 120 may not always be maintained. Although a posture does not change in a certain amount of time, the lower jaw may be moved backwards at certain time intervals. It is because fatigue and a pain of the user may increase when the forward movement of the lower jaw is always maintained during sleep. The certain time interval may be a time set by the user. Alternatively, the certain time interval may be a result value obtained when the sleep state of the user is trained by using the controller 221. Alternatively, the certain time interval may be a value that is input in advance by a provider or the user of the mandibular advancement system 10 according to an embodiment to minimize stress of the user. That is, as the lower teeth seating part 120 is moved backwards at certain time intervals while the user sleeps, the user may get sound sleep.

When the sleep position is the side lying lateral position, snoring may worsen depending on a condition of the user. In this case, the lower jaw may be moved forward through snoring sound detected by the respiration sensor 132. That is, whether to move the lower jaw forward may be determined by designated priorities of respective sensors and by collectively considering information detected from respective sensors. Operation conditions of the mandibular advancement device 100 may be arbitrarily determined in advance by the user, may be freely changed and used, or may be determined based on a learning model that is trained based on deep learning. Therefore, the operation conditions may not be applied to every person and customized and used for each individual.

Hereinafter, a mandibular advancement device 100 using a different operation type will be described.

Figure 9:
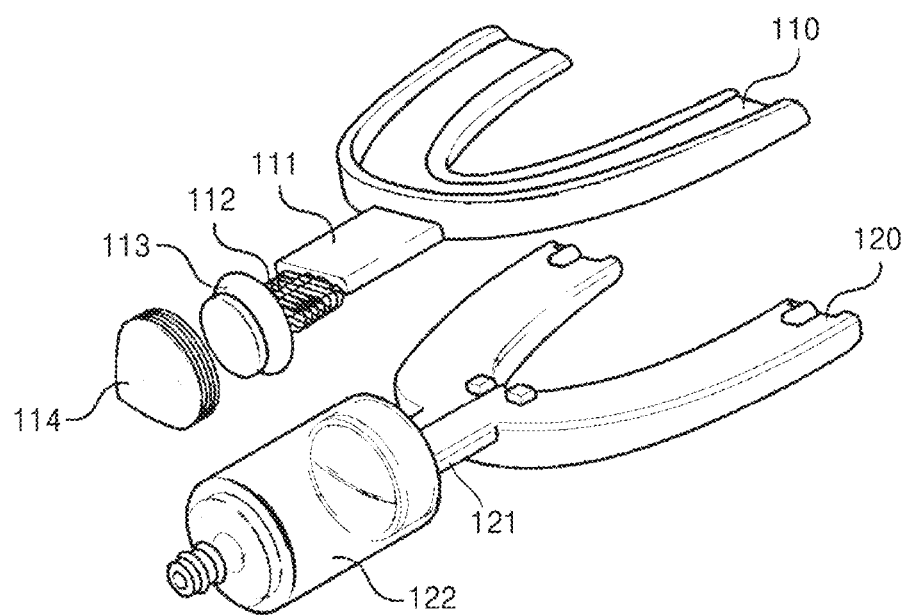
FIG. 9 is an exploded perspective view of an upper teeth seating part and a lower teeth seating part of a mandibular advancement device using a different operation type of the present disclosure.
Figure 10:
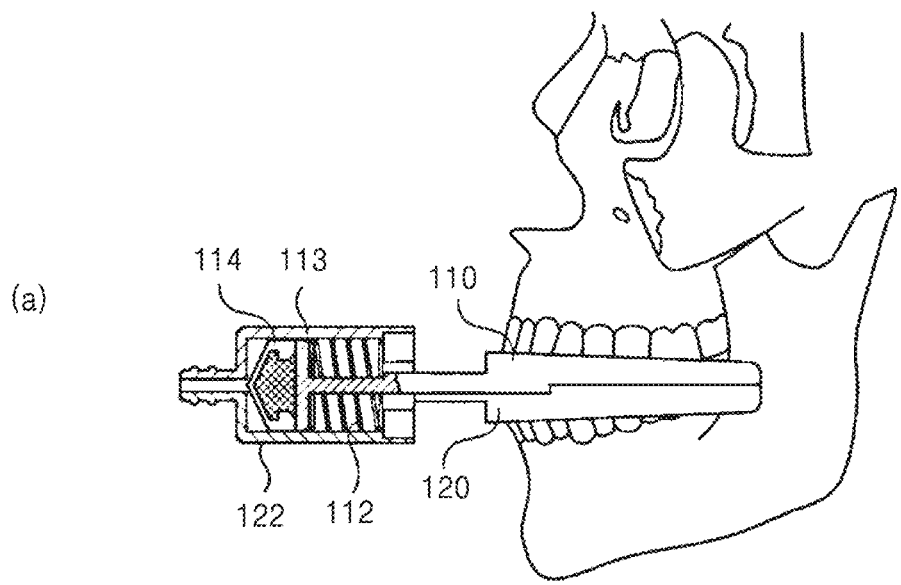
FIG. 10 is a diagram illustrating a working principle of the mandibular advancement device of FIG. 9.
Figure 10:
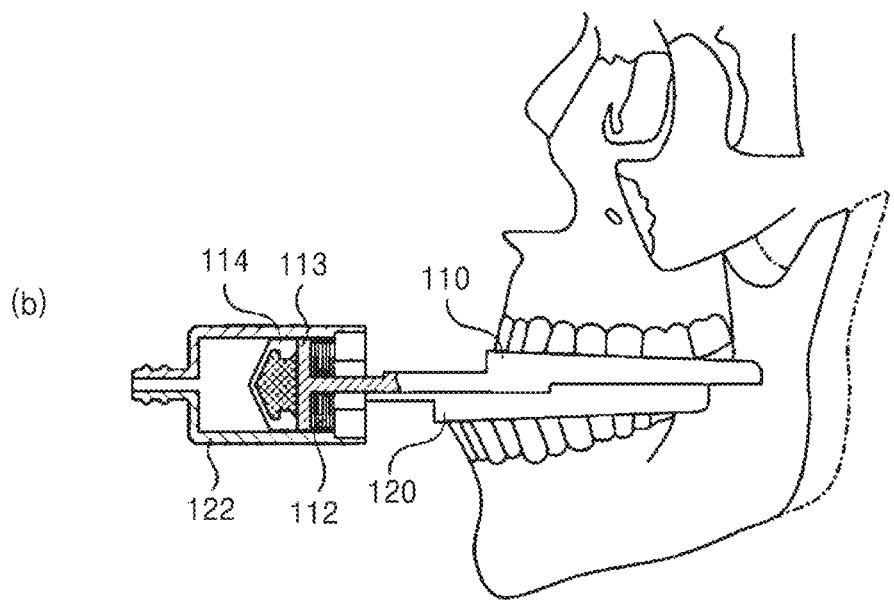
Figure 11:
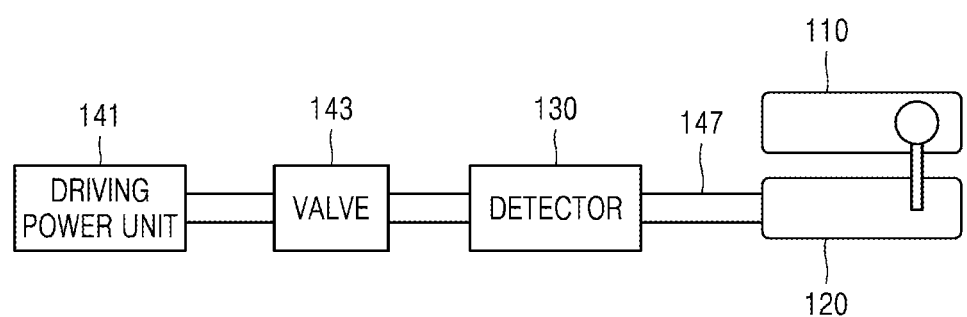
FIG. 11 is a schematic diagram of a case where a driver is of an air-pump type.

FIG. 9 is an exploded perspective view of an upper teeth seating part and a lower teeth seating part of a mandibular advancement device using a different operation type of the present disclosure. FIG. 10 is a diagram illustrating a working principle of the mandibular advancement device of FIG. 9. FIG. 11 is a schematic diagram of a case where a driver is of an air-pump type, and FIG. 12 is a schematic diagram of a case where the driver is of a wire type.

Figure 12:
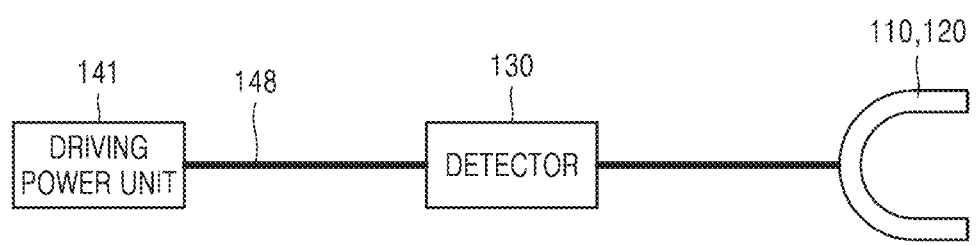
FIG. 12 is a schematic diagram of a case where a driver is of a wire type.

Referring to FIGS. 9 and 12, the driving power unit 141 of the driver 140 may include a pump used to inject air into the driving power transmission unit 145, and the driving power transmission unit 145 may include a cylinder 122 that accommodates the air injected from the pump and a piston 113 that is movable by the air from the inside of the cylinder 122.

In more detail, the upper teeth seating part 110 may be integrally connected to the piston 113 through a piston rod 111. As described above, the upper teeth seating part 110 may be connected to one end of the piston rod 111, and a sealing member 114 may be connected to one end of the piston 113. The sealing member 114 may be a rubber stopper.

The driving power transmission unit 145 may further include an elastic member 112 that provides a restoring force between the piston 113 and the cylinder 122. For example, the elastic member 112 may be a spring, and the piston rod 111 may have a shape to which the elastic member 112 may be fixed. The piston 113 connected to the upper teeth seating part 110 may prevent the upper teeth seating part 110 from being moved due to power provided by the driving power unit 141. That is, the piston 113 may fix an upper portion of the oral cavity and may function as a support to move a lower portion of the oral cavity forward.

The lower teeth seating part 120 may be integrally connected to the cylinder 122. The cylinder 122 may move the lower teeth seating part 120 forward by using the power provided by the driving power unit 141. As the cylinder 122 is moved forward, the elastic member 112 may be pressed, the elastic member 112 being disposed outside the piston rod 111. As pressed, the elastic member 112 may provide the restoring force to make the cylinder 122 be moved to a neutral position. Therefore, the pressed elastic member 112 may move the cylinder 122 to the neutral position when returning to the original position of the elastic member 112 due to the removal of the power provided by the driving power unit 141.

In the case of an air pump type, the driving power transmission unit 145 may include a tube 147 that is a passage for the air injected from the pump. The tube 147 enables the air to move towards the cylinder 122 by the power provided from the driving power unit 141. The air may be injected into the cylinder 122 through the tube 147. Also, because the lower teeth seating part 120 may be moved to the neutral position after the removal of the air injected into the cylinder 122 while the lower teeth seating part 120 is moved forward, the valve 143 may be disposed in the tube 147. Pressure of the air flowing in the tube 147 may be adjusted by the valve 143.

Also, when the mandibular advancement device 100 is of an air-pump type, the mandibular advancement device 100 may further include a pressure sensor (not illustrated) for detecting the pressure of the air in the tube 147. When the mandibular advancement device 100 is of an air-pump type, the pressure of the air in the tube 147 may increase due to the driving of the driving power unit 141, a lot of air may flow into the cylinder 122 according to an increase in the pressure of the air, and the cylinder 122 may be increasingly moved forward as the amount of air flowing into the cylinder 122 increases. Therefore, as the pressure sensor is disposed in the tube 147, signals may be transmitted to the controller 221 to appropriately adjust the pressure in the tube. That is, when the pressure in the tube 147 increases to make the lower jaw be moved forward as needed, the driving power unit 141 may stop working, and the pressure in the tube 147 may be uniformly maintained. Also, the controller 221 may open the valve 143 to decrease the pressure in the tube 147 when a decrease of snoring is identified by the respiration sensor 132 or when there is a need to make the lower jaw return to its original location.

The air pump type may operate in the following order. However, the order is not limited to that described below, and processes required by one of ordinary skill in the art may be further included between each order as appropriate.

First of all, the driver 140 may be driven. The driving of the driver 140 may indicate that power is supplied to the driving power unit 141 and the pressure of the air in the tube 147 may increase. Due to the increase of the air pressure, the air may be injected into the cylinder 122. As the pressure of the air increases, the air may be injected into the cylinder 122. In this case, power of the pressure may work in all directions except an inlet through which the air is injected. The upper teeth seating part 110 connected to the piston 113, to which the sealing member 114 adheres, may support the whole teeth. Thus, the lower teeth seating part 120 may be relatively moved forward with respect to the upper teeth seating part 110. The elastic member 112 may be pressed as the lower teeth seating part 120 may be moved forward. The pressure in the cylinder 122 may decrease through the emission of the air by opening the valve 143, and thus the lower jaw may return to the neutral position again. The restoring force of the elastic member 112 works as the pressure in the cylinder 122 decreases, and the cylinder 122 and the lower teeth seating part 120 may return to the neutral positions.

As illustrated in FIG. 12, when the driver 140 is of a wire type, the driving power transmission unit 145 may include a wire 148 instead of the tube 147. The driving power unit 141 and the cylinder 122 may be connected to each other by the wire 148. When the driving power unit 141 is of the wire type, the driving power unit 141 of the driver 140 may be a step motor. The driving power transmission unit 145 may include the wire 148. When the detector 130 transmits a signal to the controller 221 by detecting the biometric information and when there is a need to move the lower jaw forward in, for example, a supine position, the wire 148 may be moved towards the driving power unit 141. On the contrary when it is required to move the lower jaw to the neutral position in, for example, a side lying lateral position, the wire may be moved towards the user.

The driving power unit 141 may push the wire 148 to move the lower jaw to the original position, but one or more embodiments are not limited thereto. The upper teeth seating part 110 may include the elastic member 112 and receive the restoring force.

As described above, the mandibular advancement system according to one or more embodiments detects a sleep position of a patient having a snoring problem or sleep apnea and determines whether to move the mandibular advancement device according to the sleep position. Also, because the driver is disposed outside, the mandibular advancement system may decrease a pain and drooling caused when the user wears the mandibular advancement device, and may provide a sufficient amount of power to move the lower jaw forward.

While the present disclosure has been particularly illustrated and described with reference to exemplary embodiments thereof, it will be understood by those of ordinary skill in the art that various changes in form and details may be made therein without departing from the spirit and scope of the present disclosure as defined by the following claims. Therefore, the technical protection range of the disclosure will be determined by the spirit of the appended claims.

INDUSTRIAL APPLICABILITY

According to an embodiment, a mandibular advancement system for moving the lower jaw forward may be provided. Also, one or more embodiments of the disclosure may be applied to an industrially applicable technique, etc. for improving sleep apnea.

The invention claimed is:

1. A mandibular advancement system comprising:
an upper teeth seating part on which upper teeth of a user are configured to be placed;
a lower teeth seating part on which lower teeth of the user are configured to be placed;
a driver connected to the upper teeth seating part and the lower teeth seating part and configured to change a relative location of the lower teeth seating part with respect to the upper teeth seating part;
a detector configured to detect biometric information of the user; and
a controller configured to control driving of the driver based on the biometric information provided by the detector, and
a body portion comprising a surface disposed apart from the upper teeth seating part or the lower teeth seating part by a certain distance, the surface configured to correspond to a mouth portion of the user;
wherein the driver is configured to be disposed outside an oral cavity of the user and within the body portion,
wherein the detector comprises a posture sensor for detecting a movement of the user's body and a relative movement of the user's head to the user's body, and for determining a sleep position in any one of a supine position, a side lying lateral position and a prone position based on the relative positions of the body and the head,
wherein the controller is configured to control driving of the driver based on the sleep position determined by the posture sensor,
wherein, when the user's sleep position is determined to be supine, the controller is configured to determine whether the user's mandible is advanced from a first position to a second position, and if the user's mandible is advanced, the mandible is maintained in the second position, and if the user's mandible is not advanced, the mandible is advanced to the second position,
when the user's sleep position is determined to be side lying lateral or prone, the controller is configured to determine whether the user's mandible is advanced from the first position to the second position, and if the user's mandible is advanced, the mandible is returned to the first position, and if the user's mandible is not advanced, the mandible is maintained in the first position, and
wherein the controller is configured to control the driver to return the mandible when a preset time elapses in a state in which the user's mandible is advanced.

2. The mandibular advancement system of claim 1, wherein the upper teeth seating part and the lower teeth seating part are disposed outside the body portion.

3. The mandibular advancement system of claim 1, wherein the detector is located in the body portion.

4. The mandibular advancement system of claim 1, wherein the detector comprises at least any one of a respiration sensor and an oxygen saturation sensor.

5. The mandibular advancement system of claim 1, wherein the controller is configured to determine a sleep state of the user based on the biometric information and control the driving of the driver according to the sleep state.

6. The mandibular advancement system of claim 1, wherein the driver comprises a driving power unit configured to generate driving power and a driving power transmission unit configured to transmit the driving power generated by the driving power unit to the upper teeth seating part or the lower teeth seating part.

7. The mandibular advancement system of claim 6, wherein
the driving power unit comprises a pump configured to inject air into the driving power transmission unit, and
the driving power transmission unit comprises a cylinder configured to accommodate the air injected from the pump, and a piston that is movable due to the air in the cylinder.

8. The mandibular advancement system of claim 7, wherein
the driving power transmission unit further comprises a tube that is a passage for the air injected from the pump, and
the detector comprises a pressure sensor configured to detect pressure in the tube.

9. The mandibular advancement system of claim 7, wherein
the cylinder is connected to the lower teeth seating part, and
the piston is connected to the upper teeth seating part.

10. The mandibular advancement system of claim 7, wherein the driving power transmission unit further comprises an elastic member configured to provide a restoration force between the piston and the cylinder.

11. The mandibular advancement system of claim 1, wherein the posture sensor is positioned in the body portion.

* * * * *